United States Patent [19]

Del Rio et al.

[11] Patent Number: 5,601,560
[45] Date of Patent: Feb. 11, 1997

[54] TOOL BIT FOR A MOTOR DRIVEN SURGICAL INSTRUMENT

[75] Inventors: Eddy H. Del Rio, Royal Palm Beach; William E. Anspach, Jr., Palm Beach Gardens, both of Fla.

[73] Assignee: The Anspach Effort, Inc., Palm Beach Gardens, Fla.

[21] Appl. No.: 320,057

[22] Filed: Oct. 7, 1994

[51] Int. Cl.$^6$ .................................................. A61B 17/56
[52] U.S. Cl. ........................... 606/80; 606/180; 408/231
[58] Field of Search .................. 606/80, 180, 79, 606/1; 408/231, 232, 233; 433/165, 166

[56] References Cited

U.S. PATENT DOCUMENTS

| | | | |
|---|---|---|---|
| 4,978,350 | 12/1990 | Wagenknecht | 606/72 |
| 5,055,105 | 10/1991 | Hamlin et al. | 606/80 |
| 5,129,907 | 7/1992 | Heldreth et al. | 606/80 |
| 5,180,384 | 1/1993 | Mikhail | 606/80 |
| 5,219,174 | 6/1993 | Zurbrügg et al. | 606/80 X |
| 5,330,480 | 7/1994 | Meloul et al. | 606/80 |

*Primary Examiner*—Guy V. Tucker
*Attorney, Agent, or Firm*—Quarles & Brady

[57] ABSTRACT

A surgical instrument has a housing which contains a motor that drives a spindle. A tool bit is attached to the motor by a holder that includes a body with a first end portion connected to the spindle, a central portion with a cavity therein, and a second end portion having an aperture through which a shaft of the tool bit passes into the cavity. A pair of lock pawls are pivotally mounted in the cavity with each one having a first tab that enters a slot in the shaft when the lock pawls are in a first position to hold the tool bit in the instrument. The first tabs retract from the slot when the lock pawls are in a second position for changing the tool bit. The lock pawls have second tabs that engage a restrainer only in the second position to prevent the body from rotating. A ring extends around the body and pivots the lock pawls between the first and second positions when the ring moved longitudinally along the body. A manually operable shift lever is pivotally coupled to the housing and move the ring longitudinally along the body.

3 Claims, 4 Drawing Sheets

TOOL BIT FOR A MOTOR DRIVEN SURGICAL INSTRUMENT

BACKGROUND OF THE INVENTION

The present invention relates to motor driven surgical instruments; and specifically to mechanisms for releasably attaching a variety of different tool bits to the surgical instrument.

Orthopedic and neurological surgeons frequently use a power driven surgical instrument to cut, shape and drill into bone. Such an instrument utilizes a small pneumatically driven motor contained in a cylindrical housing which is held by the surgeon during use. A hose from the source of compressed air attaches to one end of housing. A tool bit is received by a fitting at the other end of the housing and is rotated by the motor when compressed air is applied to the instrument.

A wide variety of different shaped and sized tool bits are available for drilling into, cutting, and shaping bone as needed during a surgical procedure. Thus, the surgical instrument must be able to accept various kinds and sizes of tool bits.

One common surgical instrument of this type used a collet to connect an end of the tool bit shaft to the spindle of the motor. This connection required a special collet wrench in order to replace the tool bit. In addition, the various tool bits had different sized shafts thus requiring different size collets. The need for corresponding sized collets and wenches not only made tool replacement time consuming and cumbersome, it required that additional items be stocked in the operating room. Further because a sterile environment was necessary for the surgical procedure, the different collets and wrenches have to be sterilized between the procedures.

SUMMARY OF THE INVENTION

The general object of the present invention is to provide a single mechanism which is capable of attaching a variety of different sized tool bits to a power driven surgical instrument.

Another object is to provide a mechanism for attaching tool bits which does not require the use of special wrenches to change tool bits.

A further object is to eliminate the use of separate collets for each tool bit of a different size.

Yet another object of the present invention is to provide a mechanism for attaching tools which prevents the motor spindle from rotating when the instrument is not in use. This feature inhibits the tool bit from accidentally rotating when the instrument is at rest.

A powered surgical instrument includes a housing that contains a motor and a restrainer, such as a ring gear, fixedly attached to said housing. The instrument also comprises a holder for attaching a variety of different tool bits to the motor. The holder has a body within the housing with a first end portion connected to the motor for rotation about an axis, a central portion with a cavity therein, and a second end portion that has an aperture which receives tool bit shafts of various sizes.

A pair of lock pawls are pivotally mounted in the cavity. Each lock pawl includes a first tab that projects toward the axis of rotation and a second tab that projects away from the axis of rotation. When each lock pawl is pivoted into a first position, its first tab enters a slot in the shaft of a tool bit inserted into the instrument. In this state the lock pawl prevents the shaft of the tool bit from being removed from the instrument. When the lock pawl is pivoted into a second position the first tab is retracted from the shaft slot enabling the tool bit to be removed.

The second tab engages the restrainer when the lock pawl is in the second position thereby preventing rotation of the body. This enables the tool bit to be replaced without the possibility of the motor accidentally rotating the body. In the first position of the lock pawl, the second tabs are disengaged from the restrainer thus allowing operation of the instrument.

A ring extends around the body and pivots the first and second lock pawls as the ring moves longitudinally along the body. A manually operable shift lever is pivotally coupled to the housing and causes longitudinal movement of the ring along the body, thereby pivoting the first and second lock pawls.

DETAILED DESCRIPTION OF THE INVENTION

Figure 1:
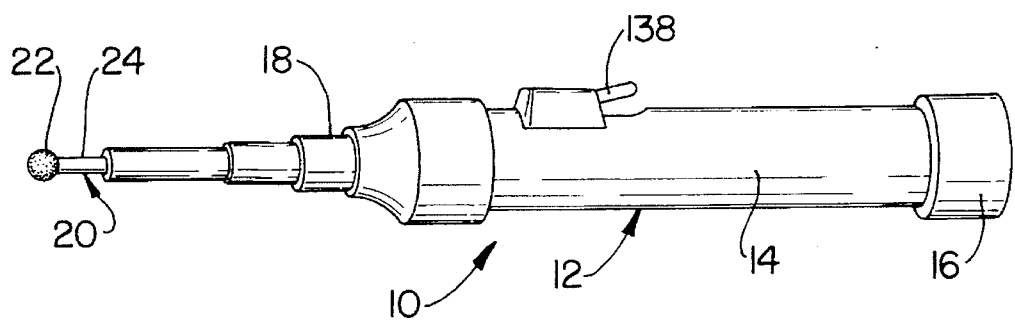
FIG. 1 is a pictorial representation of a surgical instrument according to the present invention.

Referring initially to FIG. 1, a surgical instrument 10 that incorporates the present invention has a housing 12 which encloses a pneumatic motor 14. A hose (not shown) from a source of compressed air connects to a fitting 16 at one end of the housing 12. A removable nose 18 is attached to the other end of the housing and receives an interchangeable tool bit 20. The illustrated tool bit 20 has a spherical head 22 for shaping bone during the surgical procedure. Other tool bits have cylindrical, trapezoidal and other geometrical heads depending on their intended use. The head 22 is attached to a shaft 24 that extends through nose 24 and couples to a tool holder inside housing 12.

Figure 2:
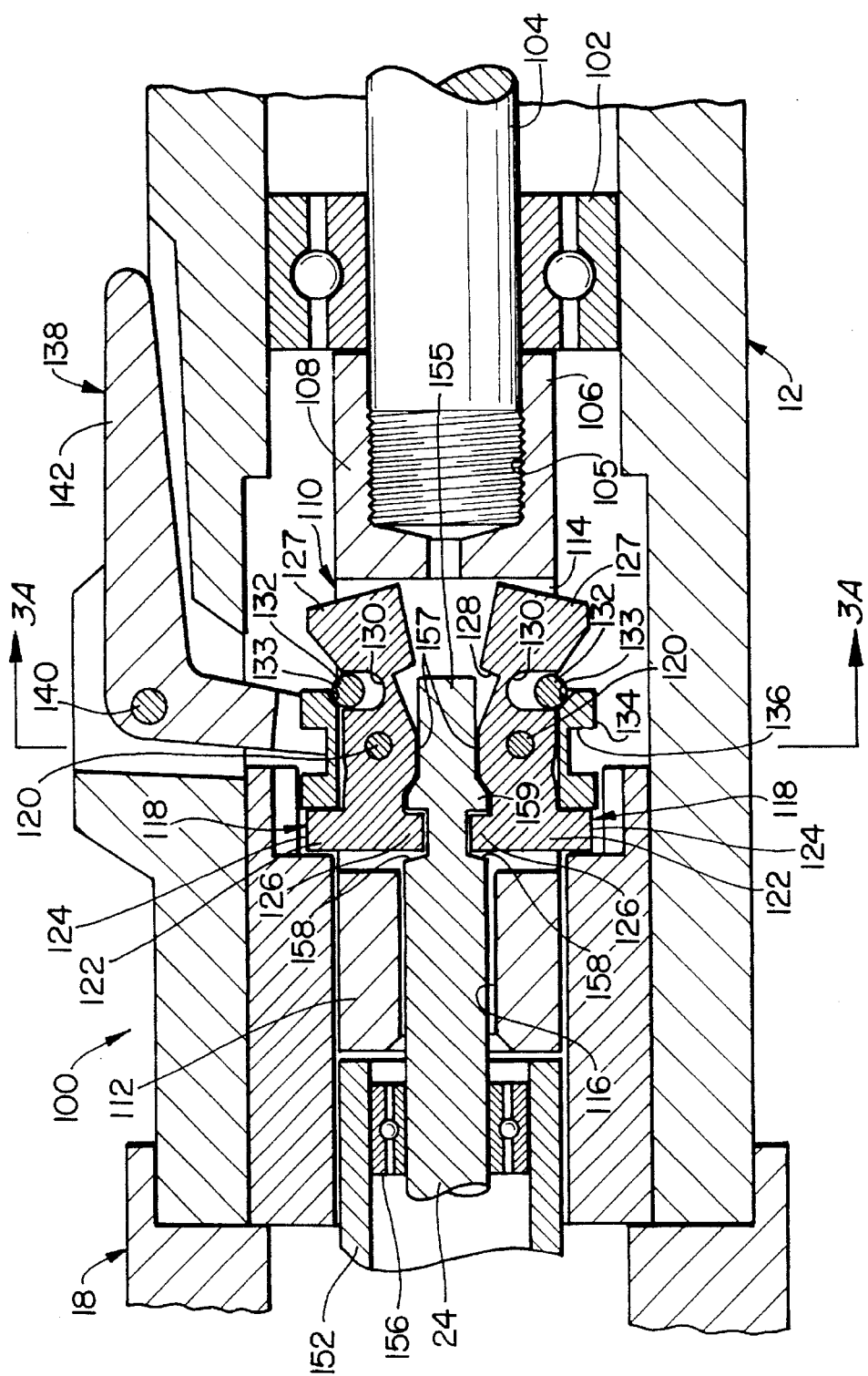
FIG. 2 is a longitudinal, cross-sectional view through a mechanism for attaching tool bits to the motor of the surgical instrument.

With reference to FIG. 2, the tool holder 100 within the motor housing 12 includes a main bearing 102 which receives the spindle 104 of the pneumatic motor 14 of the surgical instrument 10. The remote end of the motor spindle 104 has external screw threads which engage internal screw threads in an aperture 105 at one end of a lock body 106. The motor spindle 104 is attached to the lock body 106 during manufacture of the surgical instrument and remains attached thereto, except for maintenance or replacement due to failure.

The cylindrical lock body 106 has a motor coupling section 108 at the one end which attaches to the motor spindle 104. A tool receptor section 112 is located at the other end of lock body with a central portion 110 between sections 108 and 112. A slot-like, rectangular cavity 114 extends transversely through the central section 110 and occupies approximately the middle one-third of the diameter of lock body 106 (see also FIG. 3A). The tool receptor 112 has a longitudinal, centrally located aperture 116 extending from the other end of the lock body 106 to the rectangular cavity 114.

Figure 3A:
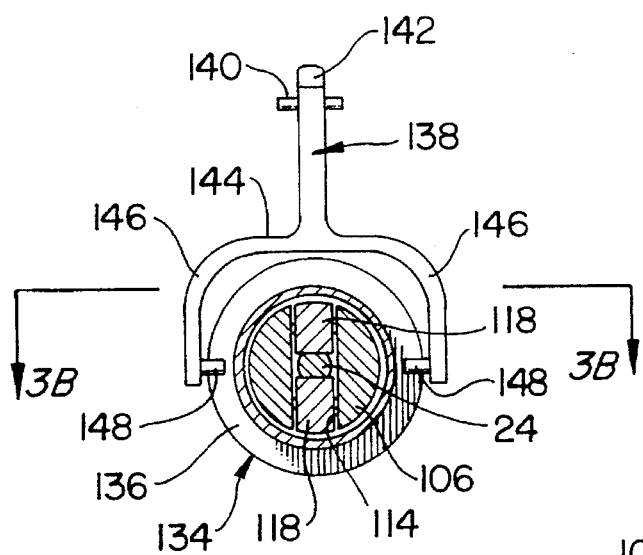
FIG. 3A is a partial sectional view taken along line 3A—3A of FIG. 2.

With reference to FIGS. 2 and 3A, a pair of lock pawls 118 are located within the rectangular cavity 114 and pivot about pawl pins 120 that extend between opposite side walls of the lock body 106 which form the rectangular cavity. Each lock pawl 118 has a cross member 122 at a first end which is adjacent to the tool receptor 112. The cross member 122 forms a T-shaped end of the lock pawl with an outer tab 124 projecting outward away from the longitudinal axis of the instrument and an inner tab 126 projecting inward toward the longitudinal axis. The opposite second end 127 of each lock pawl 118 is enlarged and has a notch 128 in its interior surface which acts as a stop during insertion of a tool bit 20 into the tool holder 100, as will be described. The outer surface of each lock pawl 118 has a notch 130 with a ball 132 freely located therein.

Figure 3B:
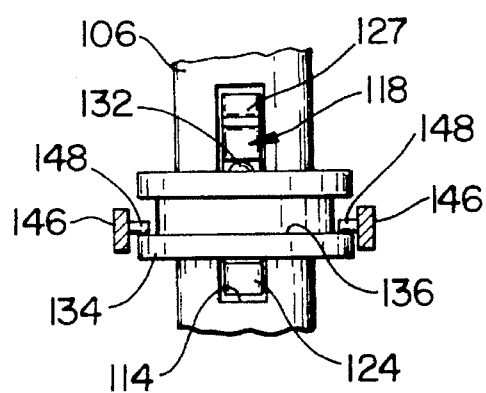
FIG. 3B is a partial sectional view taken along line 3B—3B of FIG. 3A.

An actuator, comprising a shift ring 134 and a shift lever 138, is provided to manually operate the lock pawls 118. The shift ring 134 extends around the central portion 110 of the lock body 106 and around the two lock pawls 118. The width of the shift ring is less than the distance between the cross member 126 and the second end 127 of each lock pawl 118 allowing the shift ring to move longitudinally therebetween. As will be described, the longitudinal movement of the shift ring 134 along body 106 causes each lock pawl 118 to pivot about pawl pin 120. That longitudinal movement of the shift ring 134 is produced by a shift lever 138 which rotates about a lever pin 140. The shift lever 138 has an L-shaped handle 142 with an aperture through which lever pin 140 extends. An end of the handle 142 within the motor housing 12 joins a forked section 144 of the shift lever 138, as shown in FIG. 3A. The forked section 144 has two tines 146 which curve around opposite sides of the shift ring 134. A separate pin 148 projects inwardly from the end of each tine 146 into an annular groove 136 around the shift ring 134 as shown in FIG. 3B. When the exposed end of the shift lever handle 138 is moved up and down in the orientation of the tool holder 100 in FIG. 2, the shift lever acts as a driver whereby pins 148 at the end of the tines 146 press against walls of annular groove 136 which causes the shift ring 134 to move longitudinally along the lock body 106. In the closed state of the tool holder 100 shown in FIG. 2, the shift ring 134 is pushed toward the tool receptor 112 of the lock body 106. In this position, the shift ring 134 causes the lock pawl 118 to pivot so that the cross members 122 have a generally vertical orientation with their inner tabs 126 moved toward the longitudinal axis of the lock body.

The instrument nose 18 has a tubular casing 152 with a bearing 156 located at one end thereof. The shaft 24 of the tool bit 20 extends through the nose bearing 156 and projects from the instrument nose 18 into the tool holder 100. This projecting portion of the shaft 24 extends through circular aperture 116 in the tool receptor 112 and into cavity 114 in the body 106. The outer diameter of the shaft 24 varies from tool bit to tool bit depending upon the size of the bit 22 attached to the opposite end of the shaft. The diameter of receptor aperture 116 is sized to accommodate the largest diameter shaft. The tip 155 of the shaft 24 has flat sides, thereby forming a portion of the shaft that has a polygonal cross section, and the distance between those flat sides is the same for all sizes of tools. The flat sides of the shaft tip 155 abut the flat inner surface 157 of the lock pawls 118 in the illustrated closed state of the holder 100, so that as the motor spindle 104 rotationally drives the lock body 106, torque is applied to the shaft 24 thereby rotating the tool bit 20.

The circular rod-like shaft 24 has two diametrically opposed slots 158 cut therein and spaced from the tip 155. The distance between the bottom surfaces of each slot 158 is the same for all tool bits regardless of the outer diameter of the main part of shaft 24. In the closed state of the tool holder 100 illustrated in FIG. 2, the inner tabs 126 of the lock pawls 118 enter the slots 158, acting as opposing jaws which engage an axial stop 159 formed by a rim at one side of slot 158, to securely hold the tool bit 20 from being pulled longitudinally from the tool holder 100. Thus the opposing slots 158 act as a retainer preventing removal of the tool bit. The flat inner surface of each inner tab 126 is spaced from the flat inner surface of each slot 158 so that torque is not applied to the tool bit 20 through the lock pawl tabs. In the tool bit shown in FIG. 2, the shaft tip 155 has a cross-sectional area that is greater than a cross-sectional area of the shaft portion in which slots 158 are located, and the axial stop portion 159 has a still greater cross-sectional area.

In order to reduce friction between the rotating and non-rotating components of the tool holder 100, the pins 148 on the tines of the lock lever 138 are smaller than the width of the annular groove 136 in shift ring 134. When the instrument is to be operated, the surgeon presses the shift lever 138 into the position shown in FIG. 2 and the pins engage the walls of the annular groove 136 as illustrated in FIG. 3B. The engagement of the pins forces the shift ring 134 toward the tool receptor 112, but not far enough for the shift ring to contact the outer tabs 124 on the lock pawls 118. When the instrument motor is energized by pressurized air, the spindle 104 produces rotation of the lock body 106 attached to the spindle. As the lock body spins, the balls 132 located within the notches 130 of lock pawls 118 are driven outward by centrifugal force as shown in FIG. 2. The balls 132, so driven, apply force against a beveled edge 133 of the shift ring 134, moving the shift ring further toward the tool receptor 112. This action pushes the shift ring 134 farther toward the tool receptor 112 and away from contact with the pins 148 of the shift lever 138 allowing the shift ring 134 to rotate with minimal friction.

Figure 4:
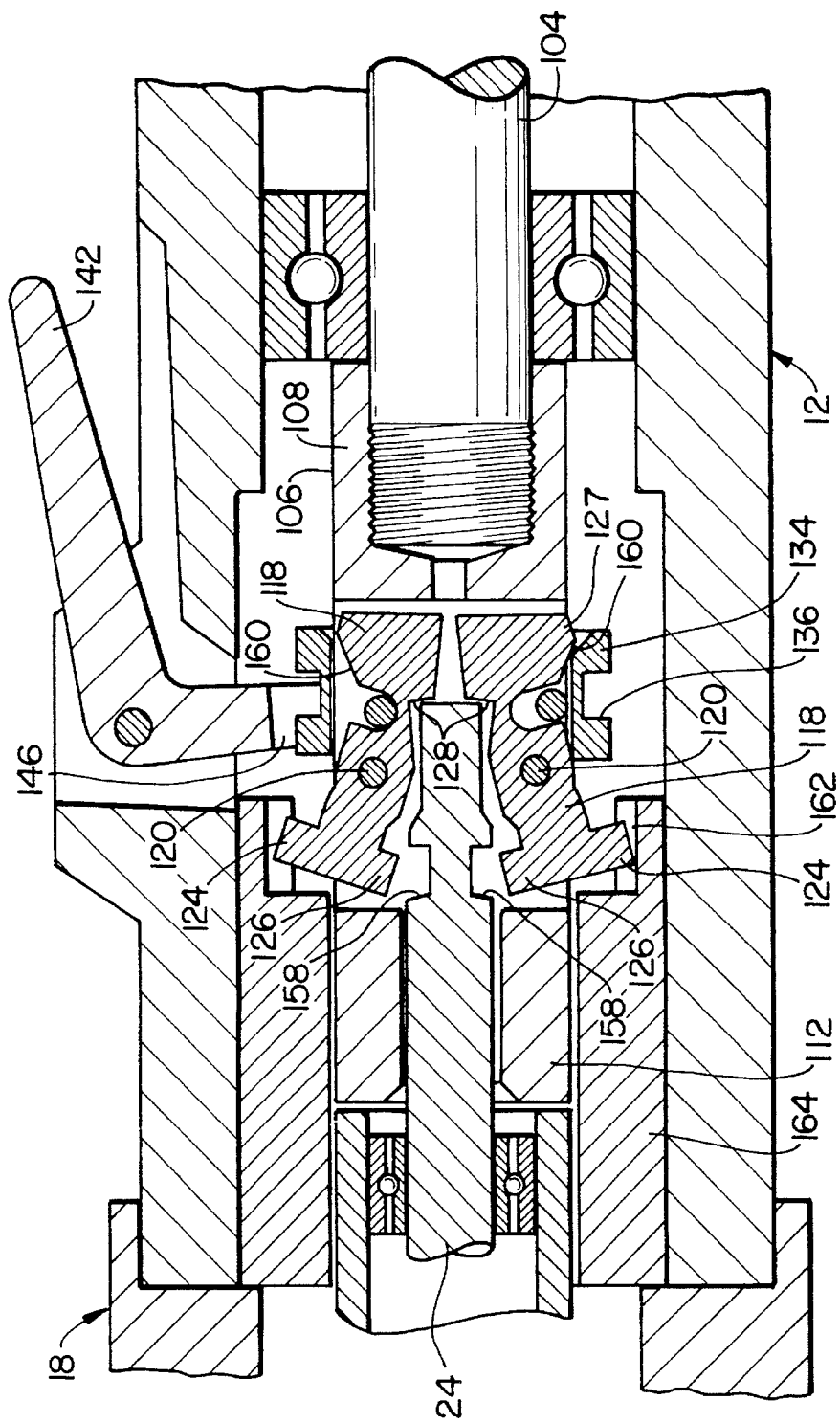
FIG. 4 is a longitudinal, cross-sectional view through the tool attaching mechanism in a different operating state.

FIG. 4 illustrates the tool holder 100 in an open state for removal or insertion of a tool bit 20. In this state, the shift lever 138 is pivoted outward from the housing 12 which causes the tine pins 148 to push the shift ring 134 toward the spindle 104. This action causes the shift ring to exert pressure against tapered surfaces 160 of each lock pawl 118 which pivots the lock pawls 118 about pawl pins 120 withdrawing the inner tabs 126 from the slots 158 in the tool shaft 24. This allows the tool shaft to be pulled out of the tool receptor 106 and the nose 18.

As each of the lock pawls 118 pivot into the position shown in FIG. 4, the outer tabs 124 engage teeth 162 of a ring gear 164 which is fixed to the casing of the tool holder 100. The ring gear 164 acts as a restrainer whereby engagement of the lock pawls 118 with the ring gear teeth prevents the lock body 106 and the shaft 24 from rotating. Thus, the surgical instrument can be placed aside without the possibility that tool bit 20 will spin should the motor be energized inadvertently.

When the tool is reinserted into the holder 100, the end of the shaft 24 contacts the stop surfaces 128 of the two lock pawls 118. This locates the shaft in the proper longitudinal position so that the inner tabs 126 of the lock pawls 118 can enter the slots 158. This engagement occurs when the shift lever is once again pushed into the casing so that the shift ring 134 slides toward the tool receptor 112 and into a position illustrated in FIG. 2. This movement of the shift ring 134 applies force to each of the lock pawls 118 causing their rotation about pawl pins 120 so that the outer tabs 124 no longer engage teeth of the ring gear.

Figure 5:
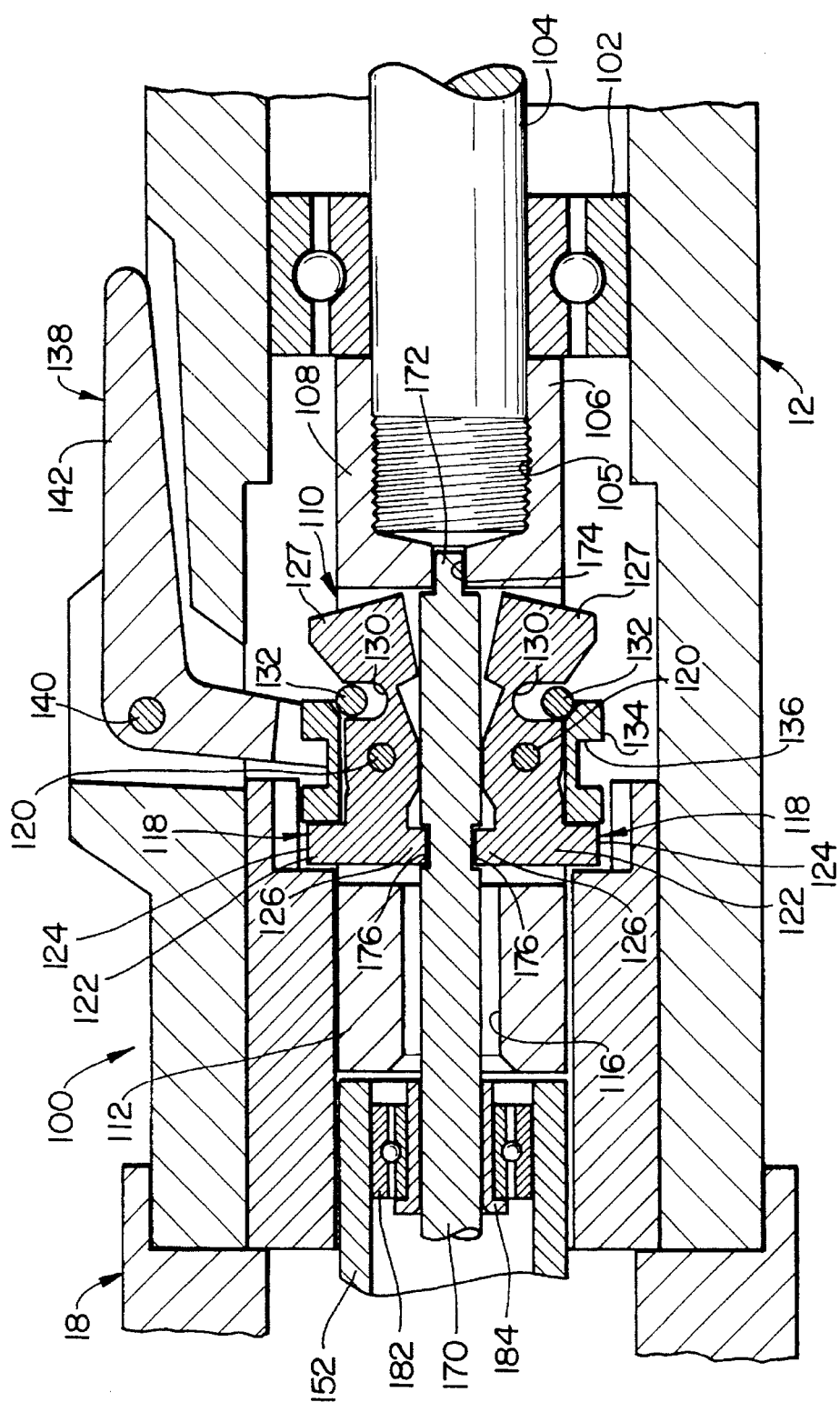
FIG. 5 is a longitudinal, cross-sectional view similar to FIG. 2 with a different size tool bit.

FIG. 5 illustrates the tool holder 100 with a relatively small tool bit attached thereto. The shaft 170 of this tool bit extends through the nose 18 and specifically through a bearing 182 with a reduction bushing 184 therewithin. The reduction bushing 184 reduces the inner diameter of the bearing 182 to support the outer diameter of shaft 170. The end of the shaft 170, that extends beyond the nose 18 into the tool holder 100, is significantly smaller in diameter than the shaft 24 of the tool bit illustrated in the previously described figures. The diameter of the shaft 170 is so small that it does not contact the surfaces of the pawls 118. Instead, this shaft 170 has an elongated end 172 with a rectangular cross section that fits within a rectangular aperture 174 in the interior wall of the lock body 106. It is the engagement of the rectangular end 172 of the shaft 170 with the rectangular aperture 174 that provides mechanical coupling between the lock body 106 and the shaft 170 to apply torque to the tool bit when the spindle 104 rotates.

The shaft 170 has a pair of diametrically opposed slots 176 cut in its external surface within which the inner tabs 126 of lock pawls 118 fit when the tool holder 100 is in the closed state. In this embodiment walls of the slots 176 act as axial stops. The positioning of the inner tabs 126 within slots 176 prevents longitudinal movement of the tool shaft 170 and thus prevents the tool bit from disengaging from the tool holder 100. It is noted that the surfaces of inner tabs 126 do not contact the tool shaft 170 in the closed state of the tool holder 100.

We claim:

1. A tool bit for a motor driven surgical instrument which has a housing and a lock pawl pivotally mounted in the housing with a tab on said lock pawl, said tool bit comprising:

a shaft having first and second ends and having an axial stop, adjacent the first end, adapted to engage the lock pawl thereby providing longitudinal axial resistance to retain the tool bit in the surgical instrument; and a bit formed at the second end of said shaft, said shaft having a first portion between the axial stop and the first end, said first portion having an outer surface, said shaft having a second portion between the axial stop and the second end, said second portion defining a pair of slots having flat surfaces adjacent the axial stop, said flat surfaces being positioned radially inwardly relative to the outer surface of said first portion.

2. The tool bit as recited in claim 1 wherein said first portion has a polygonal surface adapted to engage a torque transmission surface of the lock pawl.

3. The tool bit as recited in claim 1, wherein the shaft includes a third portion between the first portion and the first end, said third portion including a polygonal surface adapted to engage a torque transmission surface of the lock pawl, said third portion having a smaller cross sectional area than the cross sectional area of the slotted second portion.

\* \* \* \* \*